United States Patent [19]

Heine et al.

[11] 4,382,219

[45] May 3, 1983

[54] ARRANGEMENT CONSISTING OF A BATTERY HANDLE FOR ELECTRO-OPTICAL DIAGNOSTIC INSTRUMENTS, OF A CHARGER AND OF A STORAGE CELL

[75] Inventors: Helmut A. Heine; Otto H. Schmidt; Hans J. Spitschan, all of Herrsching, Fed. Rep. of Germany

[73] Assignee: Heine Optotechnik GmbH & Co. KG, Herrsching, Fed. Rep. of Germany

[21] Appl. No.: 215,558

[22] Filed: Dec. 11, 1980

[30] Foreign Application Priority Data

Feb. 29, 1980 [DE] Fed. Rep. of Germany ........ 3007831

[51] Int. Cl.³ .................... H02J 7/00; F21L 9/00; H01M 10/44
[52] U.S. Cl. ........................................... 320/2; 362/183; 429/7
[58] Field of Search .................... 320/2, 3–5, 320/25; 429/7; 362/183

[56] References Cited

U.S. PATENT DOCUMENTS 3,281,637 10/1966 Hultquist ............................ 320/2
4,147,163 4/1979 Newman et al. .................... 128/9

FOREIGN PATENT DOCUMENTS 881809 12/1959 United Kingdom .................. 320/2

Primary Examiner—R. J. Hickey
Attorney, Agent, or Firm—Woodcock, Washburn, Kurtz, Mackiewicz & Norris

[57] ABSTRACT

An improved battery handle system which provides for safe use of either a rechargeable storage cell or non-rechargeable batteries. This system comprises a battery handle adapted to hold the storage cell, having a positive pole adapted to interact with the charger to provide recharging of the storage cell as desired. The charger has a biased contact pin which makes electrical contact with the positive pole of a storage cell. However, if a battery handle with non-rechargeable batteries is inadvertently connected to the charger, the pin cannot extend sufficiently into the battery handle so as to contact the non-rechargeable batteries.

3 Claims, 5 Drawing Figures

ARRANGEMENT CONSISTING OF A BATTERY HANDLE FOR ELECTRO-OPTICAL DIAGNOSTIC INSTRUMENTS, OF A CHARGER AND OF A STORAGE CELL

BACKGROUND OF THE INVENTION

The invention relates to an arrangement or system consisting of:

a battery handle for electro-optical diagnostic instruments, one end face of the handle being provided with an aperture and the handle having a casing at least portions whereof are electrically conductive;

a charger with a connecting pin which, in the charging position, projects into the aperture of the battery handle; and a storage cell with a positive pole which protrudes from an end face thereof and, after insertion into the battery handle, projects into the aperture of the latter.

In electro-optical diagnostic instruments, for example opthalmoscopes, otoscopes and the like, in general a so-called battery handle is provided, which serves to receive a battery or a storage cell and to hold, and supply current to the instrument formed as an attachment to the battery handle. Diagnostic instruments of the said type are used, for example, in doctors' consulting rooms or in the treatment rooms of hospitals, and they are preferentially operated with handles which are fitted with storage cells. Since, due to the required convenient size of the handles, the storage cells have only a limited capacity, it is in general recommended to re-insert the handles after each examination into the chargers provided for this purpose, so that they are always ready to operate. In practical use, however, it is frequently necessary to carry out a large number of examinations with such a handle, and in certain circumstances with different diagnostic attachments, before the storage cell can be recharged. This is the case, for example, during rounds in the hospital or during home visits by the doctor. It can then happen that the capacity of the storage cell is prematurely exhausted. For this case, it is extremely advantageous if the handle is designed in such a way that the inserted storage cell can simply be exchanged for dry batteries which are not rechargeable and which later are replaced again by the rechargeable storage cell. In the event of this exchange being forgotten for once, which can readily be imagined, battery handles of this type must be designed in such a way that, if one or more batteries have been introduced into the handle, an inadvertent connection to the charger is impossible. This is necessary in order to prevent damage to the charger or an expansion or even explosion of the batteries subjected to a charging current.

In the arrangement of the type described initially, known from U.S. Pat. No. 4,147,163, the storage cell has a greater length than the batteries which can be inserted into the handle. Within the casing, on the side of the aperture of the battery handle, a contact piece is provided which is axially displaceable under the tension of a spring and which, in the case of using batteries, forms a bridge from the battery terminal towards the electrically conductive part of the casing of the battery handle and, when a storage cell is used, interrupts the connection to the conductive part of the casing because of the greater length of the storage cell.

Such a switching mechanism is relatively complicated and constructionally expensive, and this entails not only high costs but frequently also failures of the arrangement, above all because of inadequate contact being made. Furthermore, since the electrically conductive part of the casing of the battery handle in this arrangement can only be provided on the cylindrical wall part thereof, the negative pole on the storage cell must be taken out laterally with the aid of a spring contact and, due to the necessary aperture in the cylindrical part of the insulating bush of the storage cell this causes difficulties in manufacture and with respect to the mechanical durability of the storage cell.

A further disadvantage of this arrangement is that the storage cell would in any case, because of the lateral spring contact, have to have a smaller diameter than the battery types envisaged for exchange. This considerably restricts the choice of batteries and storage cells available, because of their standardized diameters.

SUMMARY OF THE INVENTION

It is the object of the invention to provide a system which consists of a battery handle and a rechargeable storage cell, the handle being adapted for connection to a charger, the system being constructed such that an inadvertent connection of the charger to the battery handle, when the handle holds non-rechargeable batteries, is prevented with certainty in as simple and reliable a manner as possible.

According to the invention, this object is achieved:

when the connecting pin of the charger is movable in the axial direction and is elastically pre-tensioned in the direction of the battery handle, when this is placed on, and protrudes, in the moved-out state, beyond the surrounding surface of the battery handle by a distance which is smaller than the axial extent of the wall surrounding the aperture of the battery handle;

when the negative electrode of the storage cell is connected to a contact ring surrounding its positive pole; and when the electrically conductive part of the casing is electrically connected to the contact ring.

First of all, moving parts in the battery handle itself are completely avoided in the arrangement according to the invention so that, in this respect, the arrangement is constructionally simple and safe to handle.

The storage call according to the invention is of simple structure and is easy to manufacture. The contact ring, provided on the end face of the storage cell and surrounding the positive pole, can readily be fitted and connected to the negative electrode of the storage cell during manufacture; the outer sheath of the storage cell can be designed in one piece without apertures.

The only moving part of the arrangement is the connecting pin of the charger, which does not cause any constructional, mechanical or electrical difficulties whatsoever. It can be moved out of the charger only to such an extent that it cannot reach the negative pole of a battery inserted into the battery handle. By contrast, the positive pole of a storage cell inserted into the battery handle projects from the interior into the aperture of the battery handle to such an extent that, after the battery handle has been inserted into the charger, the positive pole is reached by the connecting pin of the latter.

In a preferred embodiment, the surface of the battery handle, surrounding its aperture, or inner opening, is electrically conductive. In this case, the rim surrounding the aperture of the battery handle is preferably drawn inwards. In this way, an especially reliable contact between the casing of the battery handle and the negative pole of a storage cell or of a battery can be achieved.

As an alternative to this, a preferably conical compression spring is arranged concentrically to the aperture of the battery handle, which compression spring acts in the axial direction and the diameter of which corresponds, at the end located inside, to that of the contact ring. In this way, the differences in length, which are particularly large in certain types of batteries, can be reliably compensated.

In a further preferred embodiment, an insulating washer which is provided with an insulating bush surrounding the positive pole of the storage cell, is located between the positive pole of the storage cell and the contact disc connected to the negative electrode thereof, so that inadvertent short-circuits, for example due to the connecting pin of the charger, can be reliably prevented.

In a further preferred embodiment, the aperture of the battery handle is provided in a bottom cap which can be unscrewed. This construction of the handle enables batteries to be changed in a very simple manner.

BRIEF DESCRIPTION OF THE DRAWINGS

The invention is explained in more detail by reference to the illustrative embodiments represented in the drawing in which.

Figure 1:
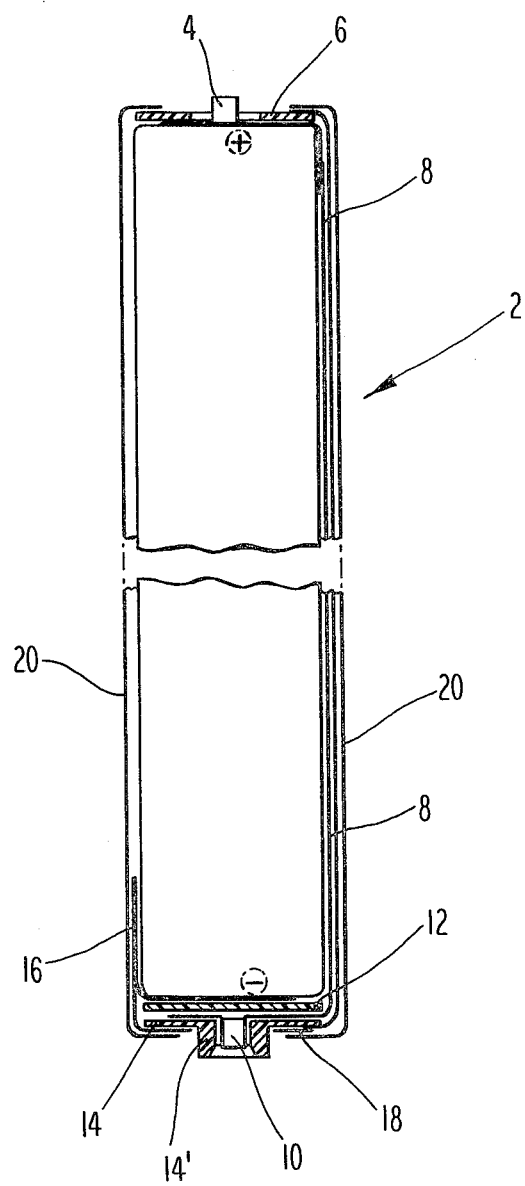
FIG. 1 shows a diagrammatic sectional view of the construction of the storage cell according to the invention.

According to FIG. 1, the storage cell 2 has a first positive pole 4 which is placed on the positive electrode thereof and which is covered by an insulating washer 6 and projects outwards through the central aperture of the latter. The positive pole of the storage cell 2 is connected, via a contact strip 8 running along the shell surface thereof, to a second positive pole 10 which is provided at the opposite end face of the storage cell 2 and which is insulated from the negative electrode of the storage cell 2 by means of an insulating washer 12. A further insulating washer 14, to which an insulating bush 14' surrounding the second positive pole 10 is moulded, is placed onto the second positive pole. A contact ring 18 which is connected via a contact strip 16 to the negative electrode of the storage cell 2, is placed onto the insulating washer 14. The shell surface of the storage cell 2, including the contact strips 8 and 16, is enclosed by an insulating sheath 20 which overlaps the insulating washer 6 at one end of the storage cell 2 and overlaps the contact ring 18 at the other end. The surface of the contact ring 18 is exposed to such an extent that it is still readily accessible from the outside and that contact can be made with a corresponding sleeve-shaped connection.

In a case where the storage cell is to be introduced in any desired position into the battery handle, an insulating washer 14 with an insulating bush 14' and a contact ring 18 are provided in a corresponding arrangement at that end of the storage cell 2 which is at the top in FIG. 1, in which case the contact strip 16 must be passed along the entire length of the storage cell 2 in a similar manner to the contact strip 8.

Figure 2:
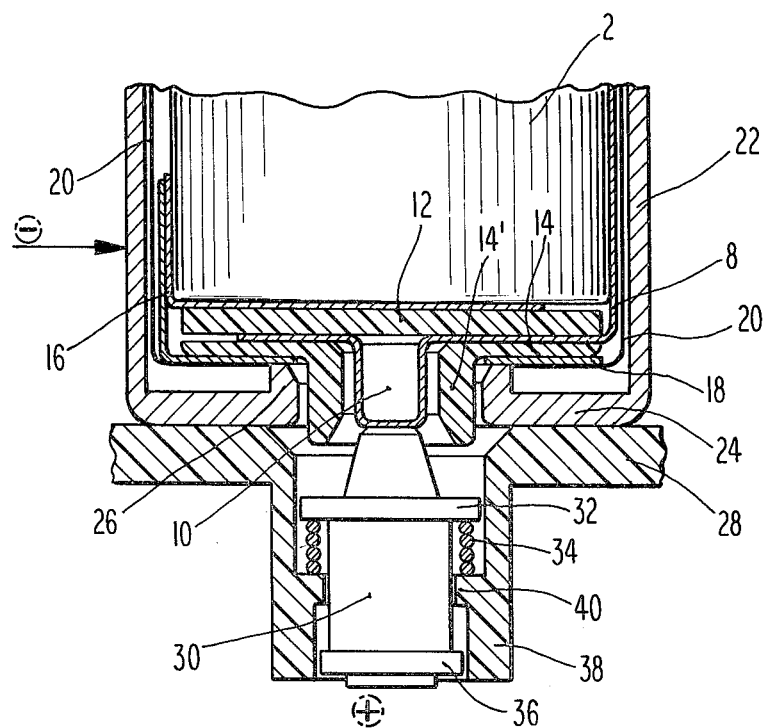
FIG. 2 shows an enlarged partial section of a battery handle, attached to a charger, with a storage cell introduced into this handle.

FIG. 2 shows an enlarged partial section of the lower end of a battery handle which houses a storage cell 2 and is inserted into the charger; likewise, only that part of the latter is shown which adjoins the battery handle.

The casing wall 22 of the battery handle is electrically conductive; the end wall 24 is provided with an aperture; the rim 26 of the end wall 24, surrounds the aperture, is drawn inwards and touches the contact ring 18 of the storage cell 2. The casing wall 28 of the charger is provided with a corresponding aperture into which the second positive pole 10 and the insulating bush 14' protrude. An axially movable connecting pin 30 with a collar 32 is located opposite the positive pole 10. The connecting pin 30 is guided in a piece of tube 38 which is moulded to the casing wall 28 of the charger and which is provided with an inward-projecting collar 40. Between the collar 32 of the connecting pin 30 and the collar 40 of the piece of tube 38, there is a compression spring 34 which pre-tensions the connecting pin 30 outwards in the axial direction. A further collar 36 which limits the outward movement of the connecting pin 30 is provided on the connecting pin 30.

When the battery handle with the storage cell 2 located therein is inserted into the charger, the connecting pin 30 connected to the positive pole of the charger is in contact with the positive pole 10 of the storage cell 2; as indicated diagrammatically by an arrow, the negative pole of the charger is connected to the electrically conductive casing wall 22 of the battery handle. Note that while pin collar 36 prevents pin 30 from moving all the way into the aperture formed by rim 26, pin 30 makes firm contact with positive pole 30 which extends out from storage cell 2.

Figure 3:
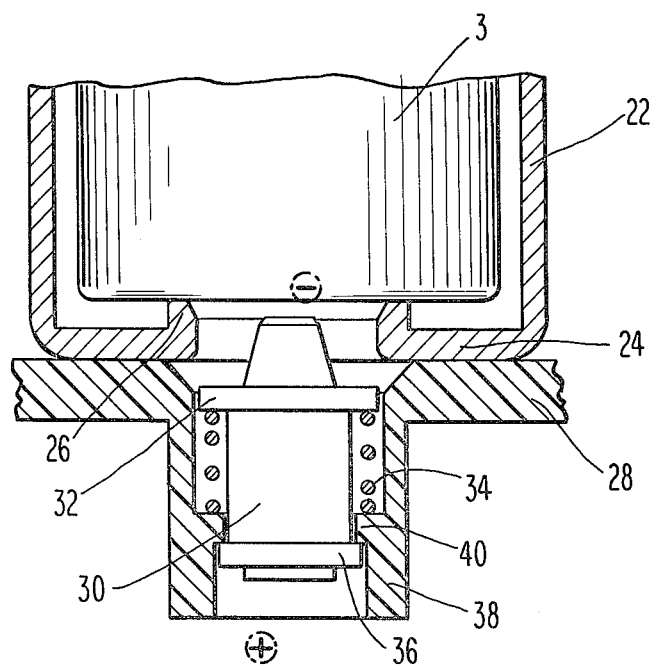
FIG. 3 shows an enlarged partial section of a battery handle, attached to a charger, with a battery introduced into this handle.

In a representation similar to that of FIG. 2, FIG. 3 shows a battery handle with a battery 3. As can be seen, the connecting pin 30 does not project into the aperture, enclosed by the drawn-in rim 26 of the battery handle, to such an extent that it reaches the negative pole of the battery 3. As illustrated, collar 36 has limited pin 30 to its fullest extension; however, this extension is less than the axial distance of rim 26, such that pin 30 does not reach the flat negative pole of the battery.

Figure 4:
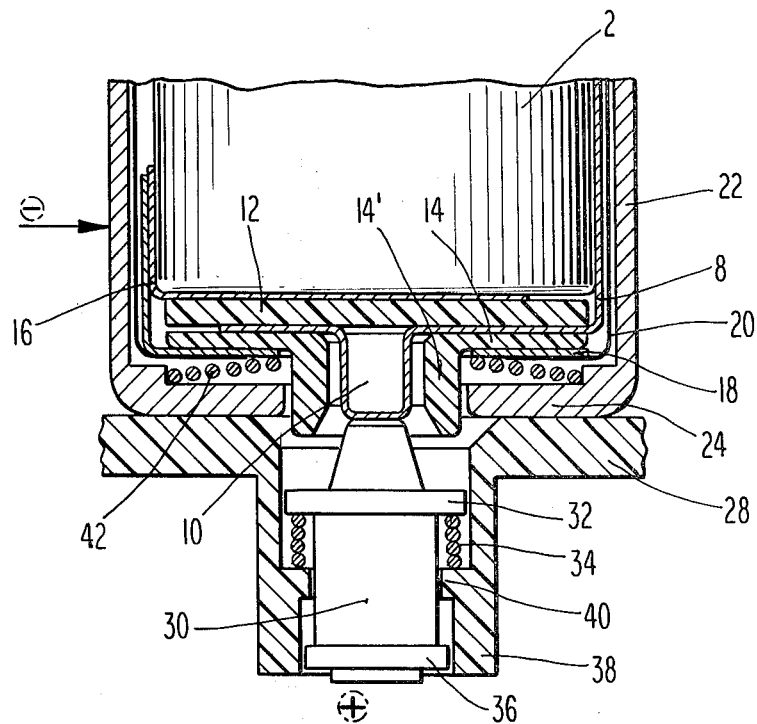
FIGS. 4 and 5 show views, similar to those of FIGS. 2 and 3, with an alternative embodiment of the connection between the battery handle and the negative pole of the battery or of the storage cell.
Figure 5:
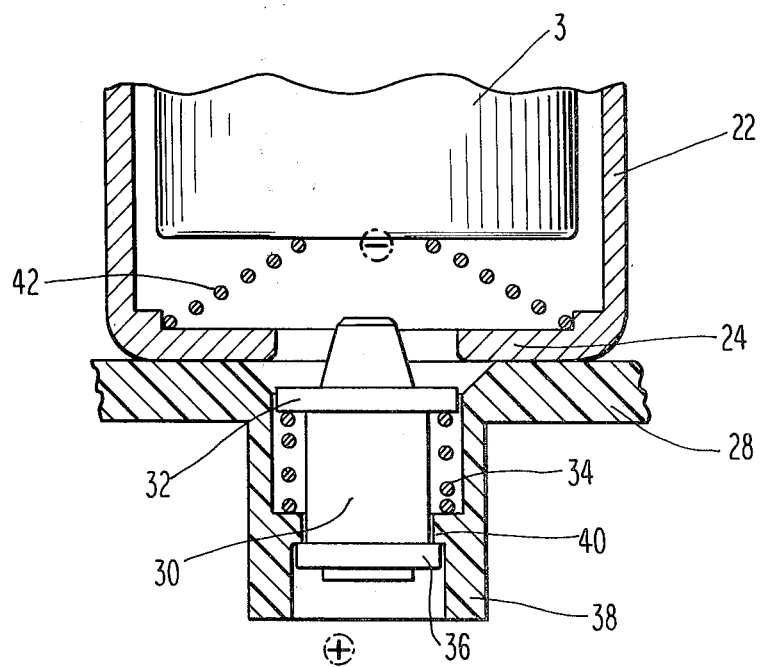

FIGS. 4 and 5 show the battery handle with an inserted storage cell 2 or battery 3, respectively. To connect the casing wall or end wall 22 or 24, respectively, of the battery 7 handle, a conical compression spring 42 is used which, according to FIG. 4, is supported on one side on the contact ring 18 and on the other side on the inside of the end wall, preferably the shoulder of a recess of appropriate dimensions. In FIG. 5, the former end of the compression spring 42 is supported on the negative pole of the battery 3.

Instead of the embodiments shown, a bottom cap which is not shown and which can be unscrewed and has an inward-drawn rim or a conical spring, can be provided at the lower end of the battery handle.

We claim:

1. A system comprising the combination of a battery handle for electro-optical diagnostic instruments, said handle housing a storage cell, one end face of said handle being provided with an aperture, said handle having a casing at least a portion of the outside surface of which is electrically conductive, charger means for charging said storage cell, having a connecting pin, said charger means being connected to said battery handle in a charging position, whereby said pin projects into the aperture of the battery handle, and said storage cell having a positive pole which protrudes from an end face thereof and, when housed in said battery handle, projects into the aperture thereof, characterized in that said handle casing has an end wall portion which defines said aperture, said connecting pin of the charging means is movable in the axial direction and is elastically pre-tensioned in the direction of said battery handle, and means limiting the movement of said pin into said aperture by a distance which is smaller than the axial extent of said end wall portion of said battery handle, and storage cell having a contact ring surrounding said positive pole and a negative electrode connected to said contact ring, and connecting means for connecting said electrically conductive part of said battery handle casing to said contact ring, and a conical compression spring which is arranged concentrically in said battery handle aperture, said spring acting in the axial direction and having a diameter which corresponds, at the end located inside, to that of said contact ring.

2. The system according to claim 1, characterized in that said battery handle aperture is provided with a bottom cap which can be unscrewed.

3. A system comprising the combination of a battery handle for electro-optical diagnostic instruments, said handle housing a storage cell, one end face of said handle being provided with an aperture, said handle having a casing at least a portion of which is electrically conductive, charger means for charging said storage cell, having a connecting pin, said charger means being connected to said battery handle in a charging position, whereby said pin projects into the aperture of the battery handle, and said storage cell having a positive pole which protrudes from an end face thereof and, when housed in said battery handle, projects into the aperture thereof, characterized in that said handle casing has an end wall portion which defines said aperture, said connecting pin of the charging means is movable in the axial direction and is elastically pre-tensioned in the direction of said battery handle, and means limiting the movement of said pin into said aperture by a distance which is smaller than the axial extent of said end wall portion of said battery handle, said storage cell having a negative electrode connected to a contact ring surrounding said positive pole, connecting means for connecting said electrically conductive part of said battery handle casing to said contact ring, said storage cell further having an insulating washer which is provided with an insulating bush surrounding said positive pole of the storage cell and located between the positive pole of the storage cell and said contact ring connected to the negative electrode thereof.

* * * * *